United States Patent [19]
Diamond

[11] Patent Number: 5,386,829
[45] Date of Patent: Feb. 7, 1995

[54] METHOD FOR ADJUSTING AN IMAGE ACCORDING TO A PRIORI PROBABILITIES

[75] Inventor: George A. Diamond, Los Angeles, Calif.

[73] Assignee: Cedars-Sinai Medical Center, Los Angeles, Calif.

[21] Appl. No.: 946,748

[22] Filed: Sep. 17, 1992

[51] Int. Cl.⁶ .................. A61B 5/00; G06K 15/22
[52] U.S. Cl. .................. 128/653.1; 364/413.02; 364/413.16; 364/413.17; 364/551.01; 364/554; 382/6; 382/39
[58] Field of Search ............... 128/653.1; 364/413.02, 364/413.16, 413.17, 413.22, 551.01, 554; 382/6, 39, 54

[56] References Cited

U.S. PATENT DOCUMENTS

| | | | |
|---|---|---|---|
| 4,844,086 | 7/1989 | Duffy | 128/731 |
| 4,916,745 | 4/1990 | Hart et al. | 382/6 |
| 5,121,338 | 6/1992 | Lodder | 364/554 |
| 5,130,936 | 7/1992 | Sheppard et al. | 364/551.01 |
| 5,199,439 | 4/1993 | Zimmerman et al. | 364/413.02 |

OTHER PUBLICATIONS

"Bayes'Theorem: A Partical Aid to Clinical Judgment for Diagnosis of Cornary-Artery Disease," Diamond, George A., M.D., Practical Cardiology, vol. 10 No. 6, May 15, 1984.
"Simplified Application of Bayesian Analysis to Multiple Cardiologic Tests," Staniloff, H. M., M.D. et al., Clin. Cardiol. 5, 630–636 (1982).
"Exercise Thailium-201 Scintigraphy in the Diagnosis and Prognosis of Coronary Artery Disease," Kotler, Todd S. and Diamond, George A., reprinted from Annals of Internal Medicine, vol. 113, No. 9, Nov. 1, 1990.
"Computer-Assisted Diagonosis in the Noninvasive Evaluation of Patients With Suspected Coronary Artery Disease," Diamond, George A., M.D. et al., J AM Coll. Cardiol, 1983.
"Application of Information Theory to Clinical Diagnostic Testing," Diamond, George A., M.D., et al., Division of Cardiology, Department of Medicine, Cedars-Sinai Medical Center, vol. 63, No. 4, Apr., 1981.

Primary Examiner—Krista M. Pfaffle
Attorney, Agent, or Firm—Pretty, Schroeder, Brueggemann & Clark

[57] ABSTRACT

The disclosed method provides a two-dimensional display of an enhanced image of measurement data from a prescribed test (e.g., a medical test), which is adjusted to incorporate information relating to a known pretest probability that a particular condition is present. The enhancement adjusts a particular parameter of the two-dimensional image, such as gray level or hue, to facilitate a more accurate evaluation of the condition.

14 Claims, 5 Drawing Sheets

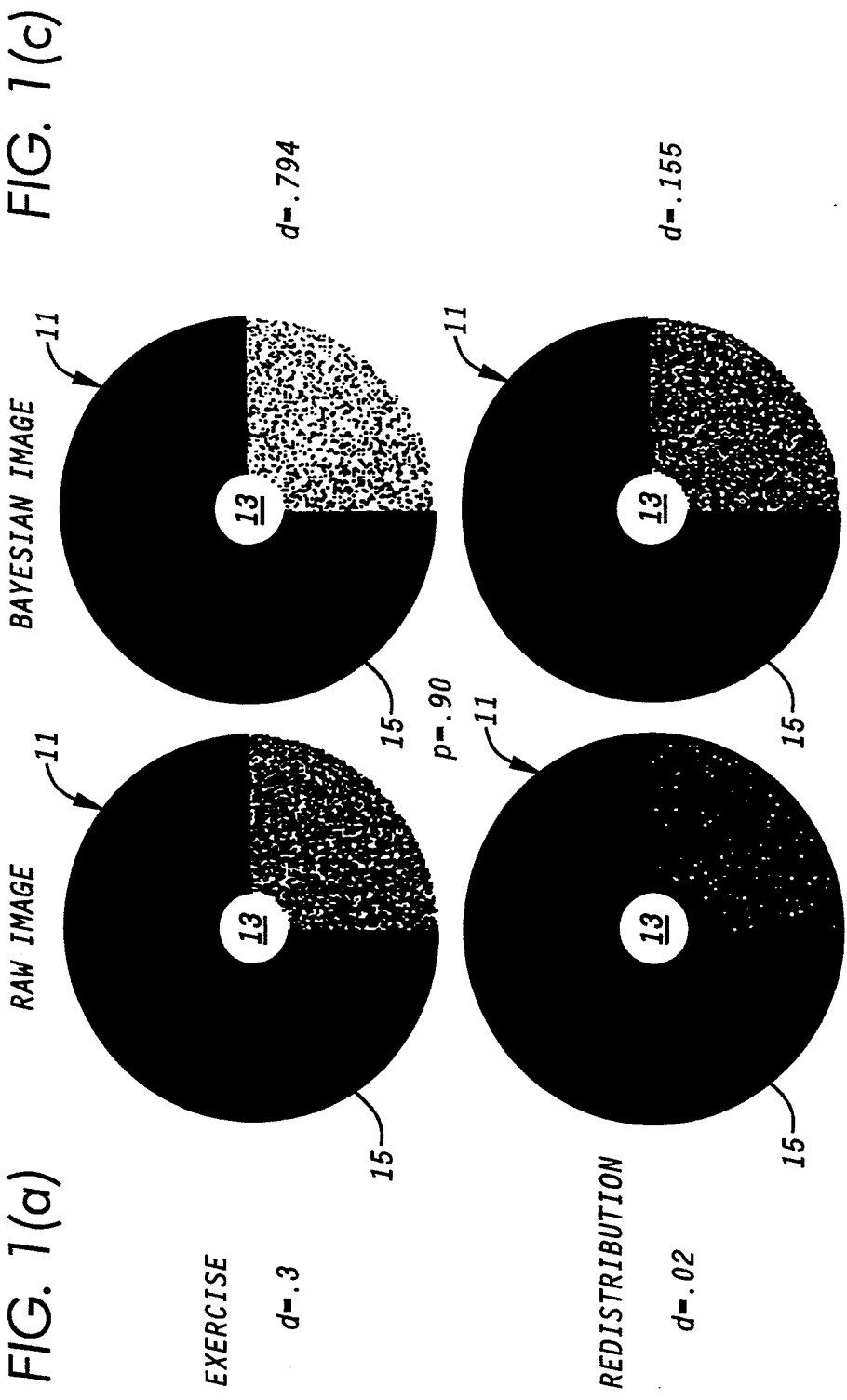

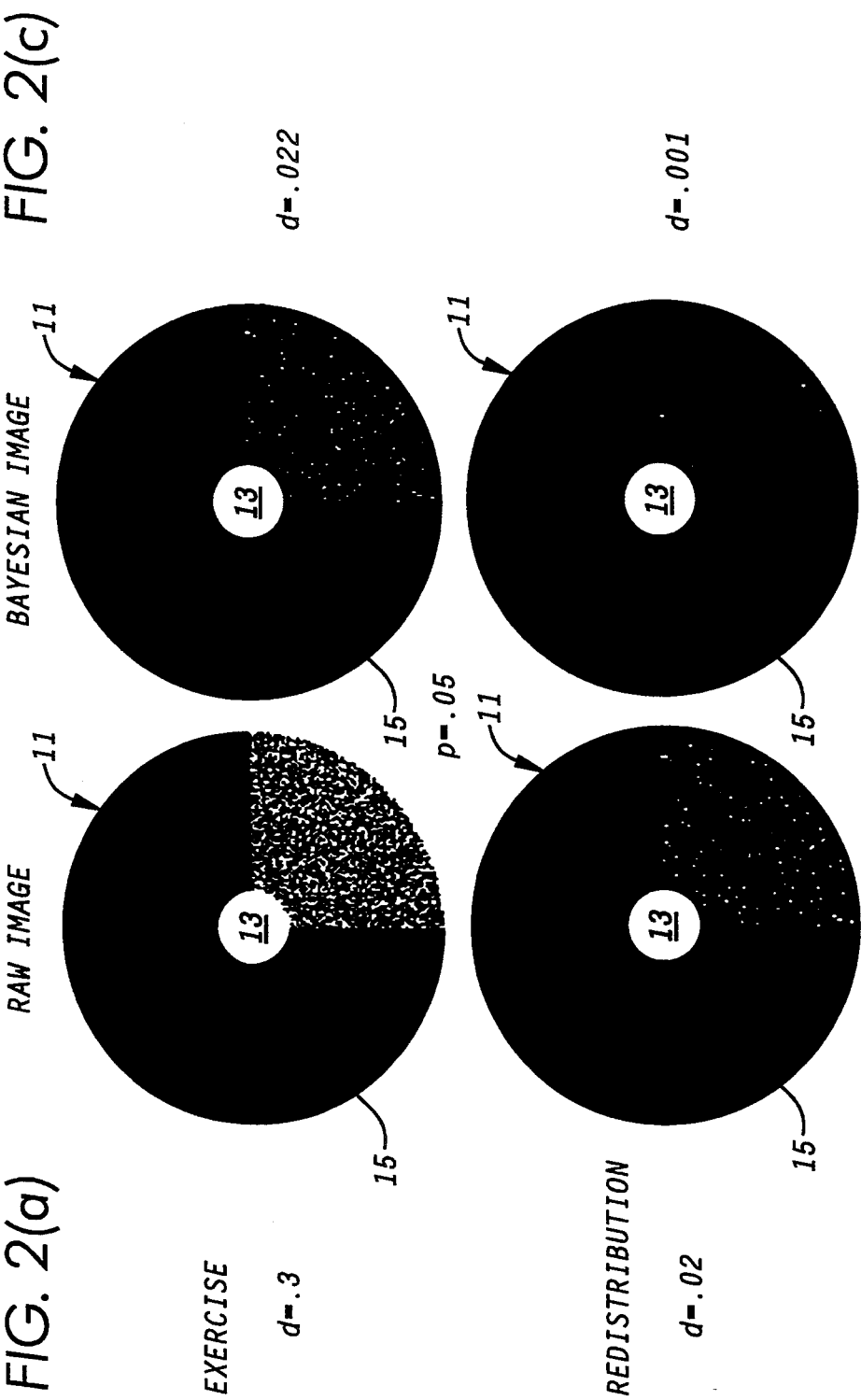

BAYESIAN AFTER IMAGE
PRETEST PROB = .95

BAYESIAN AFTER IMAGE
PRETEST PROB = .05

RAW IMAGE
PRETEST PROB = .95

RAW IMAGE
PRETEST PROB = .05

METHOD FOR ADJUSTING AN IMAGE ACCORDING TO A PRIORI PROBABILITIES

BACKGROUND OF THE INVENTION

1. Field of the Invention

This invention relates generally to methods for displaying the results of prescribed tests (e.g., medical tests administered to patients) and, more particularly, to methods that provide two-dimensional displays of such test results.

2. Description of the Related Art

In the field of medicine, diagnostic tests, prognostic tests, and functional evaluations are administered to patients to provide information that can be used by the physician to ascertain the patient's medical condition. It is recognized, however, that the results of such tests and evaluations should not be considered in isolation, but rather should be considered along with other factors pertinent to the evaluation, e.g., a pretest, or a priori, probability of a disease or condition being present. Such other factors that should be considered might include, for example, the results of earlier tests on the same patient, the patient's family history, gender, age, and so on. By taking such factors into account when evaluating the results of a test of this kind, a more accurate evaluation of the patient's condition can be made.

The need to consider pretest probabilities derives from the unfortunate fact that most medical tests are not 100% reliable in indicating whether or not a medical condition is present, or if present the extent of that condition. In almost all cases, a certain percentage of tests administered to patients actually having a disease will indicate that the disease is not present (i.e., false negatives), while a certain unrelated percentage of tests administered to patients not having the disease will result in positive test results (i.e., false positives). By making proper use of evidence indicative of pretest probabilities, the effect of those uncertainties in the significance of the test results can be minimized.

Presented below are three examples of test analyses incorporating the consideration of pretest probabilities. In the first example, the patient has a high pretest probability of having a particular disease, in the second example a low pretest probability, and in the third example an intermediate pretest probability. In all three examples, the probability of a diseased patient testing positive, i.e., the test's sensitivity, is 0.7, while the probability of a non-diseased patient testing negative, i.e., the test's specificity, is 0.9.

In the first example, a patient is selected from a group of 5000, 4500 of whom have coronary-artery disease, with at least 50% diameter narrowing of one or more major vessels. The pretest probability of disease is therefore 90%, which happens to correspond roughly to that for middle-aged men having typical angina pectoris. Because of the test's sensitivity of 0.7 and specificity of 0.9, it follows that testing all 5000 patients would lead to 0.7×4500, or 3150, true-positive test results and (1−0.9)×500, or 50, false-positive test results. Thus, 3150 of the combined 3200 positive test results would in fact be correct. This corresponds to a post-test, or posterior, likelihood of 98.4% that a positive test represents a confirmation that a particular patient is in fact diseased.

Conversely, in the case of a negative test result in this same population of 5000 patients, 4500 of whom are diseased, (1−0.7)×4500, or 1350, false-negative test results will be observed among the diseased patients, and 0.9×500, or 450, true-negative test results will be observed among the non-diseased patients. Thus, 1800 negative test results would be observed, 1350 of them being false negatives and 450 true negatives. The post-test probability of disease in a patient for whom a negative test result is obtained therefore is 75%. In other words, for a particular patient selected from this population, a negative test result indicates that that patient still has 75% probability of being diseased.

Summarizing the results of the first example, which covers a population of patients for whom the pretest probability of disease is 90%, a positive test result increases the probability of disease from 0.9 to 0.984, while a negative test result reduces the probability of disease from 0.9 to 0.75.

In the second example, the same test is administered to a population of 5000 patients, this time only 250 of whom are diseased. This corresponds to a pretest disease probability of only 5%, which is similar to that of an asymptomatic population. In this example, true-positive test results will be produced for 0.7×250, or 175, while false-positive test results will be produced for (1−0.9)×4750, or 475. The post-test probability of disease for any individual for whom a positive test is produced therefore is 175/(175+475), or 26 9%. A positive test result therefore is not particularly meaningful, since false positives outnumber true positives by a ratio of almost 3 to 1.

In the case of a negative test result, (1−0.7)×250, or 75, false-negative tests will be observed in the diseased patients, while 0.9×4750, or 4275, true-negative test results will be observed in the non-diseased patients. Thus, the post-test probability of disease in the negative test population is 75/(75+4275), or merely 1.7%.

Thus, for patients having a pretest disease probability of only 5%, a positive test result increases the probability from 5% to 26.9%, while a negative test result reduces the probability from 5% to 1.7%.

Finally, in the third example, the same diagnostic test is administered to a population of 5000, this time 50% of whom are diseased. True positive results will therefore number 0.7×2500, or 1750, while false positive results will number (1−0.9)×2500, or 250. The post-test probability of disease for a patient receiving a positive test result therefore will be 1750/(1750+250), or a 87.5%. Conversely, false-negative test responses among diseased patients will number (1−0.7)×2500, or 750, while true-negative responses among nondiseased patients will number 0.9×2500, or 2250. The post-test probability of disease for a patient with a negative test therefore will be 750/(750+2250), or 25%. The diagnostic test is therefore particularly meaningful for patients in this population, for whom the disease prevalence is 50%. Positive test results will increase the probability of disease from 50% to 87.5%, while negative test results will reduce the probability of disease from 50% to 25%.

Although the analysis described above is known in the art, it is not readily appreciated or followed by all physicians who are called upon to analyze the results of diagnostic, prognostic and functional tests and offer informed medical judgments. For one reason or another, the analysis is not properly followed. There is therefore a need for a method that makes the necessary adjustments to the results of medical tests to incorporate pretest or a priori probabilities, and to display the adjusted information in a manner that is more likely to be accepted by the evaluating physician. The present invention fulfills this need.

SUMMARY OF THE INVENTION

The present invention resides in a method for providing a two-dimensional display representative of the significance of the results of a prescribed medical test administered to evaluate the possible presence of a predetermined condition, where the display incorporates a known pretest, or a priori, probability that the predetermined condition is present, thereby facilitating a more informed evaluation. The invention has particular utility in the evaluation of a prescribed medical test administered to a patient.

More particularly, the method includes preliminary steps of determining the pretest probability that the predetermined condition is present and administering the prescribed test to generate a test measurement bearing some relationship with the condition being evaluated. This test measurement is adjusted based on the pretest probability to produce an adjusted measurement, and a two-dimensional display is then provided having a parameter that varies according to the adjusted measurement. A corresponding two-dimensional display having a parameter that varies according to the raw test measurement, as contrasted with the adjusted measurement, optionally can be provided alongside the first display, for comparison purposes. With this enhanced display, pretest probability information can more readily be incorporated into the analysis and thereby enable a more accurate evaluation to be provided.

The parameter of the two-dimensional display that is varied according to the adjusted measurement can be any of several alternatives, such as shade of gray or color, i.e., hue. In the case of a shade of gray variation, the pixels of the display's pixel array can themselves vary in shade between black and white. Alternatively, each pixel can be either black or white, with the proportion of black pixels representing the shade of gray. This latter display can be achieved by comparing the adjusted measurement for each pixel with a random number selected from an appropriate range and then displaying either a black value or a white value according to the outcome of the comparison.

The adjusted measurement produced in the step of adjusting can be a single measurement, such that the resulting display is substantially uniform across a substantial portion of its two dimensions. Alternatively, the test measurement can include a plurality of test measurement values representing a two-dimensional area. In this case, the adjusted measurement includes a plurality of adjusted measurement values, each associated with a separate test measurement value. The resulting display therefore would ordinarily be a non-uniform image, representing a section of the patient's body.

Other features and advantages of the present invention should become apparent from the following description of the preferred method, taken in conjunction with the accompanying drawings, which illustrate, by way of example, the principles of the invention.

BRIEF DESCRIPTION OF THE DRAWINGS

FIGS. 1(a)-1(d) are four schematic images of the radioactivity of a section of a patient's heart, the patient having a relatively high pretest probability of disease, with FIG. 1(a) representing the heart immediately after the injection of a thallium-201 isotope, FIG. 1(b) representing the heart several hours later, after redistribution of the isotope, FIG. 1(c) representing the heart at the same time as FIG. 1(a), but corrected to incorporate the patient's high pretest disease probability, and FIG. 1(d) representing the heart at the same time as FIG. 1(b), but again corrected to incorporate the patient's high pretest disease probability.

FIGS. 2(a)-2(d) are four schematic images similar to FIGS. 1(a)-1(d), but for a patient having a relatively low pretest probability of disease.

DESCRIPTION OF THE PREFERRED METHOD

Figure 3B:
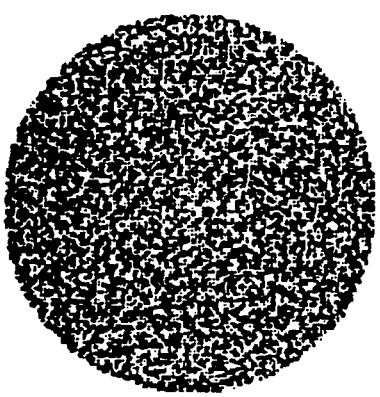
FIGS. 3(a) and 3(b) are displays of exemplary images representing a ventilation perfusion lung scan and an image representing the same scan after adjustment for the patient's high pretest probability of disease, similar to FIGS. 1 and 2, but where the images are variable across their areas.

With reference now to the drawings, and particularly to FIGS. 1(a)-1(d), there are shown displays of several images useful to a physician in diagnosing a particular condition in a patient. The images all represent a cross-section of the patient's heart 11, with a blood chamber 13 being depicted in the middle of each image and the heart muscle 15 being represented by the annular section surrounding the blood chamber. The two images of FIGS. 1(a) and 1(b) indicate the raw results of a coronary artery disease test, with the FIG. 1(a) image representing the density of an apparent defect or blockage in the heart muscle immediately after a thallium-201 isotope has been introduced, and with the FIG. 1(b) image representing the density of that apparent defect several hours later, termed a redistribution density.

In FIGS. 1(a) and 1(b), whiteness indicates the presence of the isotope in the heart muscle, whereas blackness indicates the absence of the isotope. It will be noted that the lower right quadrant of the heart muscle in this example exhibits a defect density of 30%, as compared with a normal 0% density, and that this defect density diminishes to about 2% after redistribution. In some cases, this pattern can be strong evidence of coronary artery disease.

Reliance on the images of FIGS. 1(a) and 1(b) can lead to a misdiagnosis of the patient if certain additional factors are not also considered. In particular, the a priori, or pretest, probability of this particular patient having coronary artery disease needs to be considered along with the depicted test results. The method of the invention therefore provides two additional images, shown in FIGS. 1(c) and 1(d). These images represent adjustments to the images of FIGS. 1(a) and 1(b), respectively, the adjustments being made to incorporate the known pretest disease probability for this particular patient. As such, they can aptly be called Bayesian after images, because of their reliance on Bayes Theorem. The pretest disease probability is determined based on all information known about this particular patient.

Such information might include, for example, the results of prior tests, the patient's family history, the patient's age and sex, and so on.

More particularly, the adjusted density values, or Bayesian after images, are determined by the following equation:

$$\text{Adjusted Density} = 1 - \frac{1}{\frac{\text{Raw Density}}{1 - \text{Raw Density}} \times \frac{\text{Pretest Prob.}}{1 - \text{Pretest Prob.}} + 1}$$

As used in this equation, the Raw Density term is normalized to a value between 0 and 1, with a 0 value representing a normal presence of the isotope in the heart muscle 15, and with a 1 value representing a complete absence of the isotope from the heart muscle. Consequently, the Adjusted Density term likewise has a value between 0 and 1. It will be noted that the factor Pretest Prob./(1-Pretest Prob.) is equivalent to the pretest odds of disease.

The image of FIG. 1(c) represents the adjusted defect density in the heart muscle 15 immediately after the thallium-201 isotope has been introduced, while the image of FIG. 1(d) represents the adjusted defect density after redistribution. In this example, the patient has a pretest disease probability of 0.9, and the apparent defect density immediately after introduction is adjusted from a raw value of 0.30 to an adjusted value of 0.79, while the apparent defect density after redistribution is adjusted from a raw value of 0.02 to an adjusted value of 0.16. It will be appreciated that for this particular patient a significant redistribution of the isotope is depicted, and a diagnosis of coronary artery disease being present probably is indicated.

FIGS. 2(a)-2(d) are similar to FIGS. 1(a)-1(d), and the identical raw test results depicted in FIGS. 1(a) and 1(b) are duplicated in FIGS. 2(a) and 2(b). However, the images of FIGS. 2(c) and 2(d) depict the adjusted measurements, or Bayesian after images, that would result for a patient having a very low pretest probability of having coronary artery disease, in this case only 5%. The initial raw defect density value of 30% is therefore reduced to 2.2%, while the redistribution defect density value of 2% is reduced to 0.1%. Thus, the diagnosing physician would more likely appreciate that the redistribution evidenced in FIGS. 2(a) and 2(b) images is more likely due to a false positive test result and not due to a true positive test result evidencing coronary artery disease.

FIGS. 1(a)-1(d) and 2(a)-2(d) include displays of images that are substantially uniform across large sections of their two-dimensional areas. Such images are provided when the diagnostic test being administered yields just a single value representative of the disease or medical condition being tested. A more complex situation exists where a variable two-dimensional image is generated in the test. An example of the image data generated in such a test is provided in FIGS. 3(a) and 3(b).

Figure 3A:
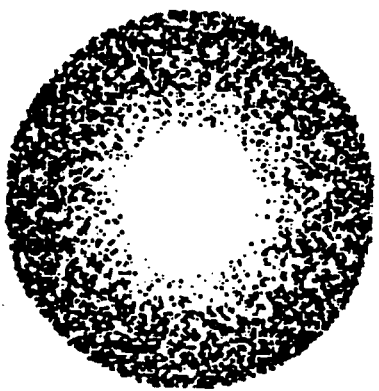

FIG. 3(a) represents the raw scan data derived from scanning a section of a patient. This could represent, for example, a thermogram of a section of the patient's skin or a ventilation perfusion lung scan. One defect will be noted, in the middle of the depicted section. Examining only FIG. 3(a) raises the question of whether or not this defect represents a true positive indication of a particular disease or merely a false positive indication for a non-diseased patient. Knowledge of the pretest disease probability for this particular patient is essential to properly evaluate the information and thereby properly diagnose the patient's condition.

The invention therefore provides an adjusted image, or Bayesian after image, depicted in FIG. 3(b), which provides an enhanced view of the patient's condition. In this example, the patient's pretest disease probability, as determined by factors such as prior test results, gender and age, is known to be 0.95. Consequently, the adjusted image provides an enhanced representation of the defect.

Figure 4B:
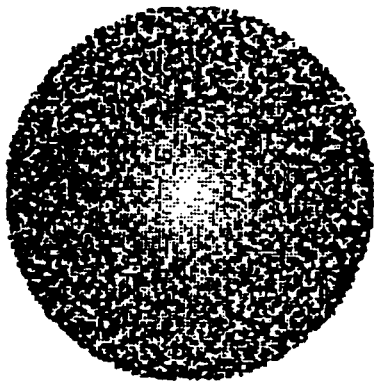
FIGS. 4(a) and 4(b) are displays of exemplary images similar to FIGS. 3(a) and 3(b), but for a patient having a relatively low pretest probability of disease.
Figure 4A:
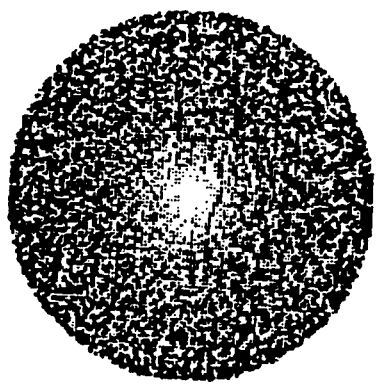

FIGS. 4(a) and 4(b) are similar to FIGS. 3(a) and 3(b), and the raw test results depicted in FIG. 3(a) are duplicated in FIG. 4(a). However, the image of FIG. 4(b) is an adjusted image, or Bayesian after image, that would result for a patient having a very low pretest probability of only 0.05. The adjusted image provides a diminished representation of the defect.

Figure 5:
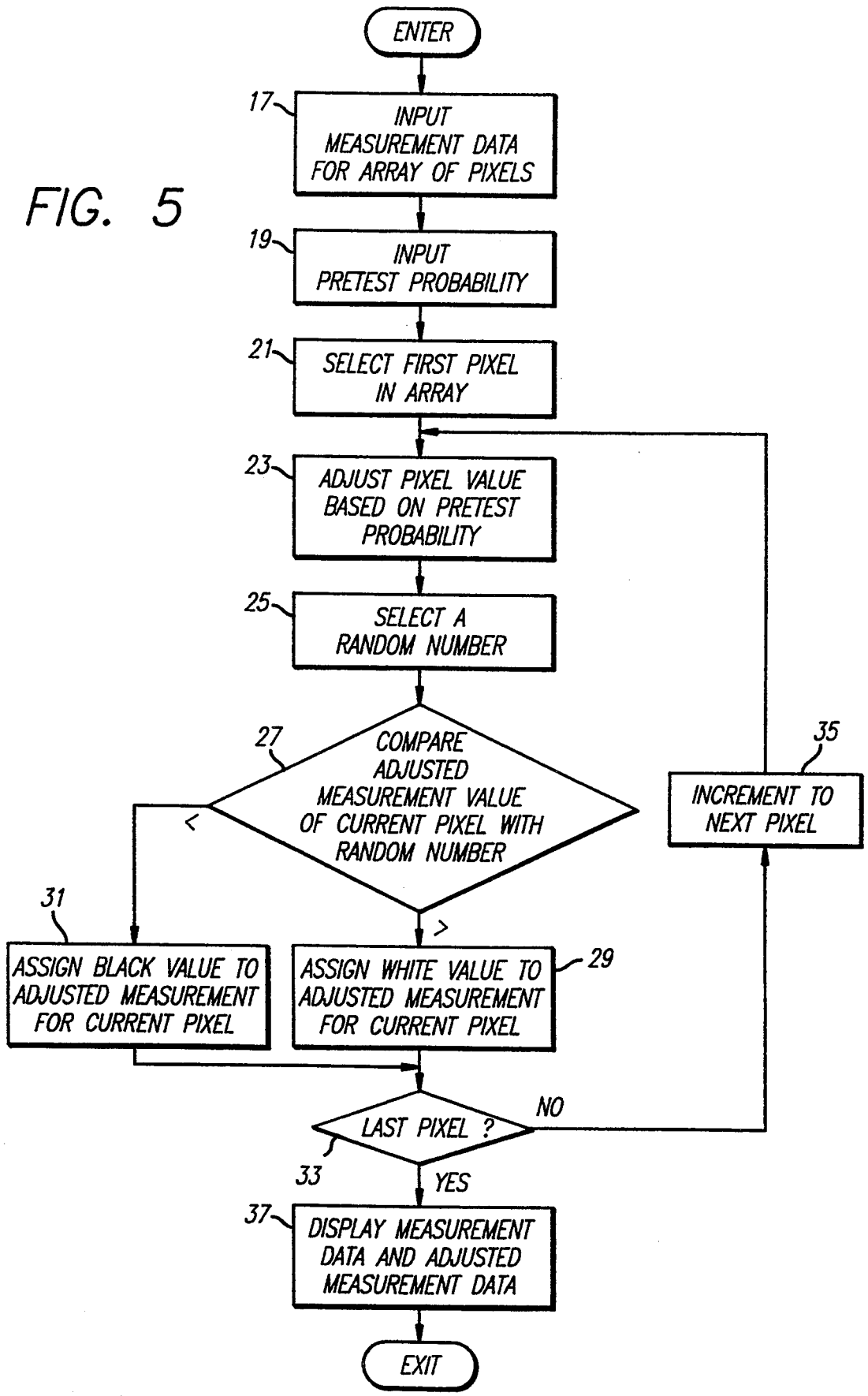
FIG. 5 is a simplified flowchart of the steps performed in the preferred method of the invention, in generating the exemplary displays set forth in FIGS. 3(a) and (b) and 4(a) and (b).

The images depicted in FIGS. 3(a) and (b) and 4(a) and (b) are produced by a system implementing a computer program like that represented by the flowchart of FIG. 5. In an initial step 17 of the program, measurement data for a two-dimensional array of pixels is input into a memory, with the data representing, for example, a two-dimensional ventilation perfusion lung scan. This data corresponds to that depicted in the exemplary image of FIG. 3(a). In a subsequent step 19, the pretest probability of this particular patient having the disease or medical condition in question is input into memory. Thereafter, in step 21, the value of the first pixel in the input measurement data is selected for processing. In step 23, this measurement value is adjusted to reflect the pretest disease probability for this particular patient, using the equation set forth above.

In a subsequent step 25, a random number is selected from a range that spans the range of interest for the measurement data. Thereafter, in step 27, the measurement value and the adjusted value computed in step 23 for the currently selected pixel are both compared with the selected random number. In each case, if the pixel value exceeds the random number, a white intensity is selected, in step 29, to be displayed for the current pixel. Conversely, if the pixel value does not exceed the random number, a black intensity is selected, in step 31, to be displayed for the current pixel. This is performed for both the raw measurement value for this pixel and the adjusted measurement value for this pixel.

An inquiry is then made, in step 33, as to whether or not the pixel just evaluated in the last pixel in the array. If not, the next pixel in the array is selected at step 35, and the processing loop is rejoined at the step 23 of adjusting the measurement value. If, on the other hand, it is determined at step 33 that the last pixel has been processed, the program advances to a final step 37 of displaying the array of adjusted measurement values (e.g., FIG. 3(b)) alongside the array of raw actual measurement values (e.g., FIG. 3(a)).

It will appreciated that the adjusted measurement values can be made to represent an image of selected resolution less than that of the images of FIG. 3(b) or FIG. 4(b). This can be useful when diagnosing some diseases. In such a modified embodiment, the adjusted value for each pixel that is compared with a random number would be substituted by the average of the adjusted values for a small array of pixels centered on the pixel in question. Such a modification would tend to provide a softer, filtered image.

It also will be appreciated that displays having parameters other than black and white values could alternatively be provided. For example, the value of each pixel, representing either a test measurement value or an adjusted measurement value, could be displayed directly on a gray scale monitor. Alternatively, the value of each pixel, again representing either a test measurement value or an adjusted measurement value, can be represented on the display as a particular hue in the range of violet to red. In another example, the display could take the form of a histogram.

Further, it will be appreciated that a series of two-dimensional displays could be provided, each representing a different section of the patient's body. Together, the series of two-dimensional displays would represent a three-dimensional image of the patient's body.

In some cases it is desirable to adjust the overall brightnesses of the two displayed images (e.g., FIGS. 3(a) and (b)) to be equal. This is done so that the physician examining the raw and adjusted images can more readily observe the detailed effects of the Bayesian adjustment, without being distracted by differences in the overall brightnesses of the images.

Figure 6:
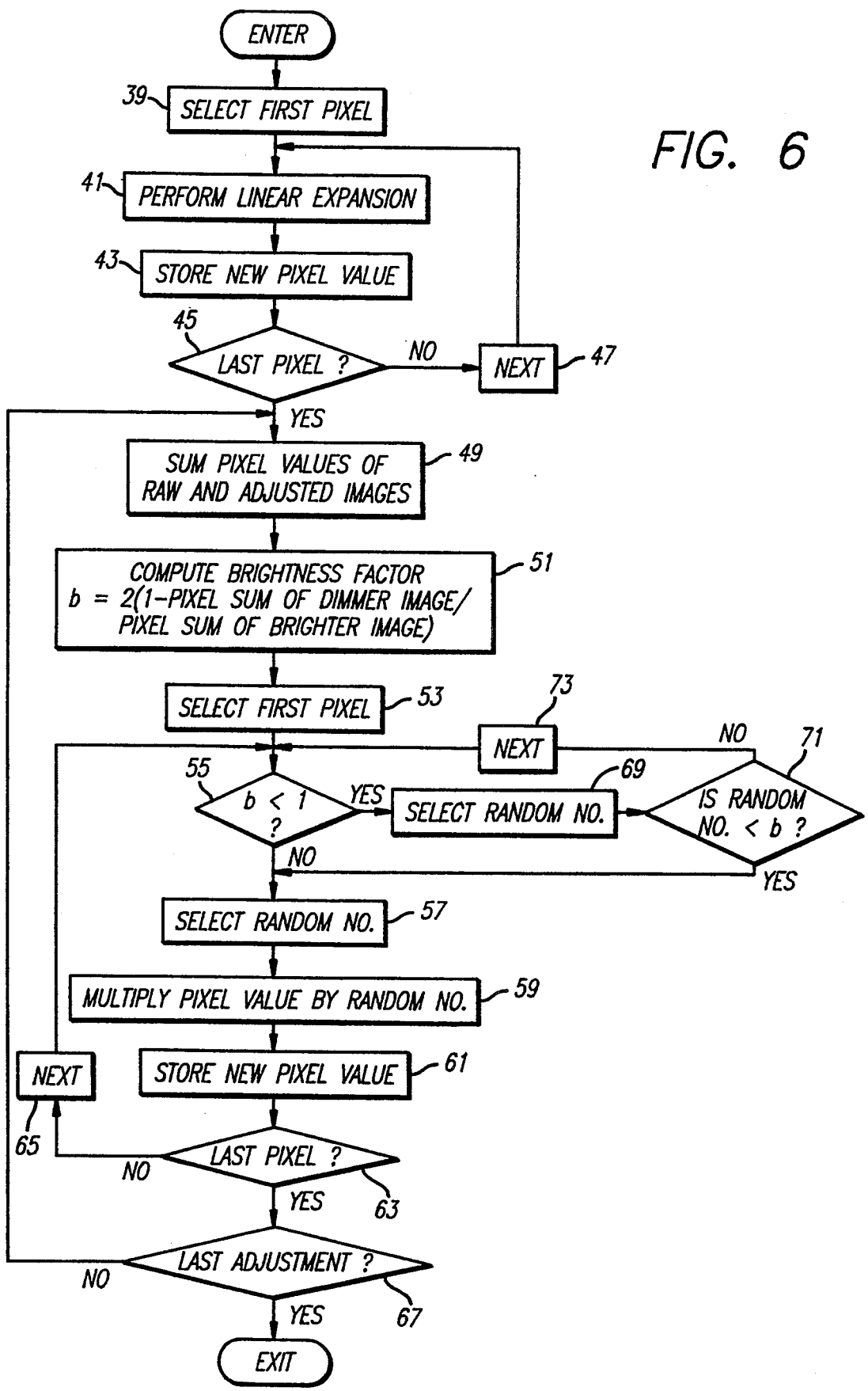
FIG. 6 is a simplified flowchart of the steps performed in an optional subroutine for equalizing the overall brightness levels of adjacent displays of raw and adjusted images.

Such a brightness adjusted can be made using a computer program subroutine like that represented by the flowchart of FIG. 6. The depicted subroutine includes two principal sections. In the first section, the pixel values are expanded back to the full dynamic range of 0.0 to 1.0. In the second section, the overall brightness of the brighter of the two images (i.e., either the raw image and the Bayesian-adjusted image) is adjusted downwardly to match that of the dimmer image. These adjustments are made on a pixel-by-pixel basis.

Thus, in an initial step 39 of the subroutine of FIG. 6, the first pixel in the array of Bayesian-adjusted image data is selected. That value is then adjusted, in step 41, according to a linear expansion formula that expands the data back to the full dynamic range of 0.0 to 1.0. This adjusted value for the first pixel is stored in step 43, and, in step 45, it is determined whether or not the pixel just adjusted is the last pixel in the image. If not, the pixel number is incremented by one, at step 47, and the program returns to step 41, in which the same linear expansion is performed on the next pixel value.

Eventually, it will be determined at step 45 that the last pixel in the Bayesian-adjusted image has been expanded, at which time the program will proceed to step 49, in which the pixel values are summed for all of the pixels in the raw image and all of the pixels in the adjusted image. These two sums are measures of the overall brightnesses of the two images. Thereafter, a brightness factor "b" is computed for the pair of images. In particular, this brightness factor is defined by the following formula:

$$b = 2\left(1 - \frac{\text{Brightness of Dimmer Image}}{\text{Brightness of Brighter Image}}\right)$$

Thus, the brightness factor b approaches the value 2.0 if the brightness of the brighter of the two images greatly exceeds the brightness of the dimmer image. The brightness factor b is equal to 1.0 if the brighter image is exactly twice as bright as the dimmer image, and is equal to 0.0 if the brightnesses of the two images are the same.

Thereafter, in step 53, the first pixel in the brighter of the two images (i.e., the raw image or the Bayesian-adjusted image) is selected for further processing. Next, in step 55, it is determined whether or not the brightness factor b is less than 1.0. If it is not, meaning that the brighter image is more than twice as bright as the dimmer image, then the program will reduce the overall brightness of that brighter image by a factor of two. This could be done by simply halving all of the pixel values. However, a preferred approach is to reduce the pixel values by random amounts that, on average, constitute a halving. This better preserves contrast in the image.

Thus, if it is determined in step 55 that the brightness factor b is not less than 1.0, the program proceeds to step 57, in which a random number between 0.0 and 1.0 is selected. The selected pixel value (selected in step 53) is then multiplied by this random number in step 59, and the resulting product is stored in step 61. Thereafter, in step 63, it is determined whether or not the pixel last processed is the last pixel in the image. If not, the pixel number is incremented by 1, in step 65, and the program returns to the step 55 of determining whether or not the brightness factor b is less than 1.0. The program then proceeds through this same loop, adjusting the second and subsequent pixels as described above. It therefore will be appreciated that this loop effectively reduces the image's overall brightness by a factor of 2.

When it is determined in step 63 that the last pixel in the image being adjusted has been processed, the program proceeds to step 67, in which it is determined whether or not the final required adjustment to the brighter image has been made, i.e., whether or not the brightness factor b is equal to 0.0, meaning that the raw and Bayesian-adjusted images are of equal overall brightness. If it is determined in step 67 that that condition has not yet been reached, the program returns to step 49, in which the pixel values for the unadjusted image and for the newly-adjusted image are summed. A new brightness factor b is then computed in step 51 for these two images. The first pixel in the brighter image is then selected, in step 53, and, in step 55, it is again determined whether or not the newly-computed brightness factor b is less than 1.0. If it again is not less than 1.0, the program proceeds through steps 57–67, as described above.

Eventually, a new brightness factor b will be computed in step 49 that is less than 1.0. When that condition is reached, the brighter image will have an overall brightness that is less than twice the overall brightness of the dimmer image. One final set of adjustments will then need to be made to the pixels in the image. Thus, the program proceeds to step 69, in which a random number between 0.0 and 1.0 is selected. If that selected random number is less than the brightness factor b, as determined in step 71, then the program proceeds to steps 57–67, as described above. This process is repeated for each pixel. If it is determined at step 71 that the selected random number is less than the brightness factor b, no change is made to the current pixel value and the program increments to the next pixel, in step 73, and returns to the step 55 of determining whether or not the brightness factor b is greater than or equal to 1.0. Another pass is then made through the steps 69 and 71. It will be appreciated that this procedure is performed on a percentage of pixels in the overall image corresponding to the value of the brightness factor b. Thus, if b is 0.9, then 90% of the pixels are so adjusted. And they are adjusted, as described earlier, by a factor that on average is one-half.

After all of the pixels have been processed for the case in which the brightness factor b was determined (in step 55) to be less than 1.0, then the newly-stored pixel values will necessarily have the same overall brightness as that of the original image. After this has occurred, it will be determined in step 67 that the last adjustment has been made. The subroutine is then exited.

The raw density images further can be calibrated with respect to the implicit sensitivity and specificity of the test being administered for a given anatomic region, by reference to the distribution of raw density values in that region among a group of patients with disease and a group of patients without disease. The so-calibrated raw density would be equivalent to the proportion of non-diseased patients with the same observed density values divided by the sum of the proportion of non-diseased and diseased patients with the same observed density values.

From the foregoing description, it should be apparent that the present invention provides a two-dimensional display of an enhanced image of the measurement data from a diagnostic or prognostic test or a functional evaluation, which is adjusted to incorporate information relating to a known pretest probability that the patient has a particular disease or condition. The enhancement adjusts a particular parameter of the two-dimensional image, such as gray level, to provide the evaluating physician with more representative information of the patient's likely condition.

Although the invention has been described in detail with reference only to the presently preferred method, those of ordinary skill in the art will appreciate that various modifications can be made without departing from the invention. Accordingly, the invention is defined only by the following claims.

I claim:

1. A method for providing a two-dimensional display representative of the significance of the results of a prescribed test administered to evaluate the possible presence of a predetermined condition, the method comprising the steps of:
   determining a pretest probability that the predetermined condition is present;
   administering a prescribed test to generate a test measurement bearing a predetermined relationship to the predetermined condition;
   adjusting the test measurement based on the pretest probability determined in the step of determining, to produce an adjusted measurement; and
   providing a first two-dimensional display having a parameter that varies according to the adjusted measurement.

2. A method as defined in claim 1, wherein:
   the method further includes a step of providing a second two-dimensional display having a parameter that varies according to the test measurement; and
   the variable parameter of the first and second two-dimensional displays are the same.

3. A method as defined in claim 1, wherein:
   the two-dimensional display provided in the step of providing is a black-and-white image; and
   the step of providing includes a step of varying the shade of gray of the two-dimensional display according to the adjusted measurement.

4. A method as defined in claim 3, wherein:
   the two-dimensional display provided in the step of providing is a video display having an array of pixels; and
   the step of providing includes steps, performed for each pixel of the display, of providing a random number and comparing that random number with the adjusted measurement corresponding to that pixel, and then displaying either a black value or a white value based on the outcome of the comparison.

5. A method as defined in claim 1, wherein:
   the adjusted measurement produced in the step of adjusting is just a single measurement; and
   the display provided in the step of providing is substantially uniform across a substantial portion of its two dimensions.

6. A method as defined in claim 1, wherein:
   the test measurement generated in the step of administering includes a plurality of test measurement values representing a two-dimensional area;
   the adjusted measurement produced in the step of adjusting includes a plurality of adjusted measurement values, each associated with a separate test measurement value; and
   the display provided in the step of providing represents a non-uniform image.

7. A method as defined in claim 6, wherein:
   the predetermined condition whose possible presence is being evaluated is a predetermined medical condition in a patient; and
   the two-dimensional display provided in the step of providing represents an image of a portion of the patient's body.

8. A method as defined in claim 6, wherein:
   the method further includes a step of providing a second two-dimensional display having a parameter that varies according to the test measurement values;
   the two-dimensional displays provided in the two steps of providing are black-and-white images and the two steps of providing include steps of varying the shades of gray of the two-dimensional displays according to the respective test measurement values and adjusted measurement values; and
   the method further includes a step of adjusting the two displayed images to have substantially the same overall brightnesses.

9. A method as defined in claim 1, wherein:
   the test measurement is scaled to have a value between 0 and 1; and
   the step of adjusting implements the following equation $$\text{Adjusted Meas.} = 1 - \frac{1}{\frac{\text{Test Meas.}}{1 - \text{Test Meas.}} \times \frac{\text{Pretest Prob.}}{1 - \text{Pretest Prob.}} + 1}.$$

10. A method for providing a two-dimensional display of a section of a patient's body and representative of the significance of the results of a prescribed medical test administered on the patient possibly having a predetermined medical condition, the method comprising the steps of:

determining a pretest probability that the patient has a predetermined medical condition;

administering a prescribed medical test on the patient to generate a test measurement bearing a predetermined relationship to the predetermined medical condition, wherein the test measurement is scaled to have a value between 0 and 1;

adjusting the test measurement based on the pretest probability determined in the step of determining, to produce an adjusted measurement, wherein the adjustment is made according to the following $$\text{Adjusted Meas.} = 1 - \cfrac{1}{\cfrac{\text{Test Meas.}}{1 - \text{Test Meas.}} \times \cfrac{\text{Pretest Prob}}{1 - \text{Pretest Prob}} + 1} \text{; and}$$

providing a video display having a gray level that varies according to the adjusted measurement.

11. A method as defined in claim 10, wherein the step of providing a video display includes steps, performed for each pixel of the display, of providing a random number and comparing that random number with the adjusted measurement corresponding to that pixel, and then displaying either a black value or a white value based on the outcome of the comparison.

12. A method as defined in claim 10, wherein:

the adjusted measurement produced in the step of adjusting is just a single measurement; and the display provided in the step of providing is substantially uniform across a substantial portion of its two dimensions.

13. A method as defined in claim 10, wherein:

the test measurement generated in the step of administering includes a plurality of test measurement values representing a two-dimensional area;

the adjusted measurement produced in the step of adjusting includes a plurality of adjusted measurement values, each associated with a separate test measurement value; and the video display provided in the step of providing represents a non-uniform image.

14. A method as defined in claim 13, wherein:

the method further includes a step of providing a second two-dimensional display having a parameter that varies according to the test measurement values;

the two-dimensional displays provided in the two steps of providing are black-and-white images and the two steps of providing include steps of varying the shades of gray of the two-dimensional displays according to the respective test measurement values and adjusted measurement values; and the method further includes a step of adjusting the two displayed image to have substantially the same overall brightnesses.

* * * * *